US00PP32100P2

(12) United States Plant Patent
Berlin

(10) Patent No.: US PP32,100 P2
(45) Date of Patent: Aug. 18, 2020

(54) ***DRACAENA* PLANT NAMED 'PVDRALC'**

(50) Latin Name: *Dracaena fragrans*
Varietal Denomination: PVDRALC

(71) Applicant: Fino Follaje S.A., San Jose (CR)

(72) Inventor: Erick Berlin, San Jose (CR)

(73) Assignee: Fino Follaje S.A., Porton de Iberia (CR)

( * ) Notice: Subject to any disclaimer, the term of this patent is extended or adjusted under 35 U.S.C. 154(b) by 0 days.

(21) Appl. No.: 16/602,582

(22) Filed: Nov. 5, 2019

(51) Int. Cl.
*A01H 5/00* (2018.01)
*A01H 6/12* (2018.01)

(52) U.S. Cl.
USPC ..... Plt./383

(58) Field of Classification Search
USPC ..... Plt./383
CPC ..... A01H 5/00; A01H 6/12
See application file for complete search history.

*Primary Examiner* — Annette H Para
(74) *Attorney, Agent, or Firm* — Samuel R. McCoy, Jr.

(57) ABSTRACT

A new and distinct *Dracaena* plant named 'PVDRALC' which is characterized by a compact growth habit and a relatively short plant height, dark green foliage born on a single unbranched stem, relaxed foliage which is heavily curled downward, foliage with a relatively high length to width ratio, and the stability of these characteristics from generation to generation.

3 Drawing Sheets

Latin name of the genus and species: The Latin name of the genus and species of the novel variety disclosed herein is *Dracaena fragrans.*

Variety denomination: The inventive cultivar of *Dracaena* disclosed herein has been given the variety denomination 'PVDRALC'.

BACKGROUND OF THE INVENTION

Parentage: 'PVDRALC' is a spontaneous whole-plant mutation of *Dracaena fragrans* 'Steudneri' plant (not patented) which was discovered at a commercial greenhouse in San Jose, Costa Rica in 2017. The mutation was initially noted for its compact habit and dark green foliage with a greater length to width ratio relative to the parent and other commercial varieties. Said mutation was isolated for further evaluation to confirm the uniformity and stability of the unique characteristics first observed. Upon confirmation of the stability and uniformity of the characteristics, the new plant was selected for commercialization.

Asexual Reproduction: Asexual reproduction of 'PVDRALC' is accomplished by way of rooting stem cuttings. Propagation was first performed in 2017 at the inventor's commercial greenhouse in San Jose, Costa Rica. Through two subsequent generations, the unique features of this cultivar have proven to be stable and true to type.

SUMMARY OF THE INVENTION

The cultivar 'PVDRALC' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PVDRALC'. These characteristics in combination distinguish 'PVDRALC' as a new and distinct *Dracaena fragrans* cultivar:

1. *Dracaena* 'PVDRALC' exhibits compact growth habit with a relatively short plant height; and
2. *Dracaena* 'PVDRALC' exhibits very dark green foliage born on a single dark green, unbranched stem; and
3. *Dracaena* 'PVDRALC' exhibits relaxed foliage which is heavily curled downward; and
4. *Dracaena* 'PVDRALC' exhibits foliage with a relatively high length to width ratio compared to the parent and other commercial varieties.

BOTANICAL DESCRIPTION OF THE PLANT

Figure 1:
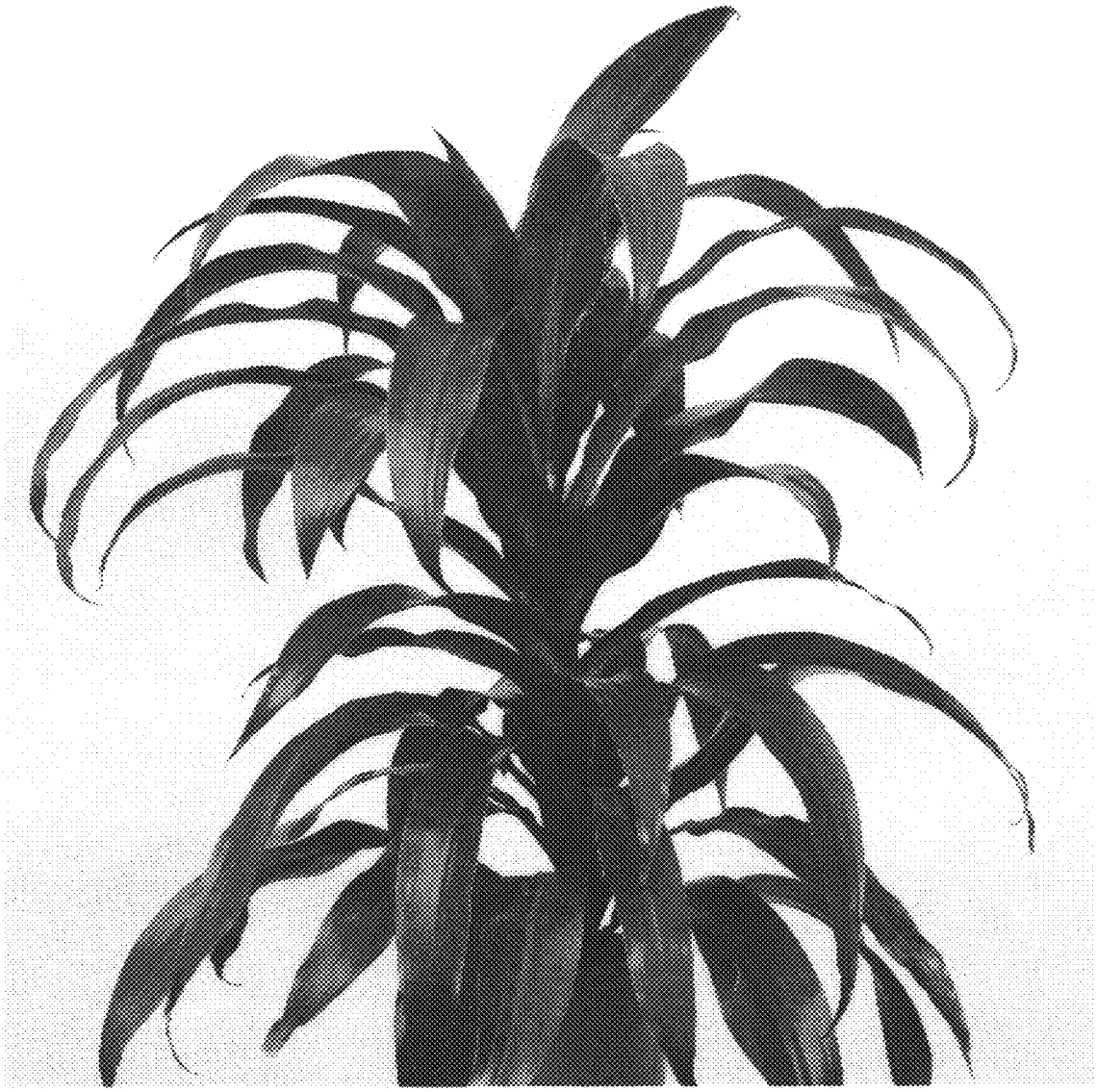
FIG. 1 illustrates, as nearly true as it is reasonably possible to make the same in color photographs of this type, an exemplary plant of 'PVDRALC' grown in San Jose, Costa Rica. This plant, grown in a 15 cm nursery container, is approximately 26 weeks old from a rooted young plant.
Figure 2:
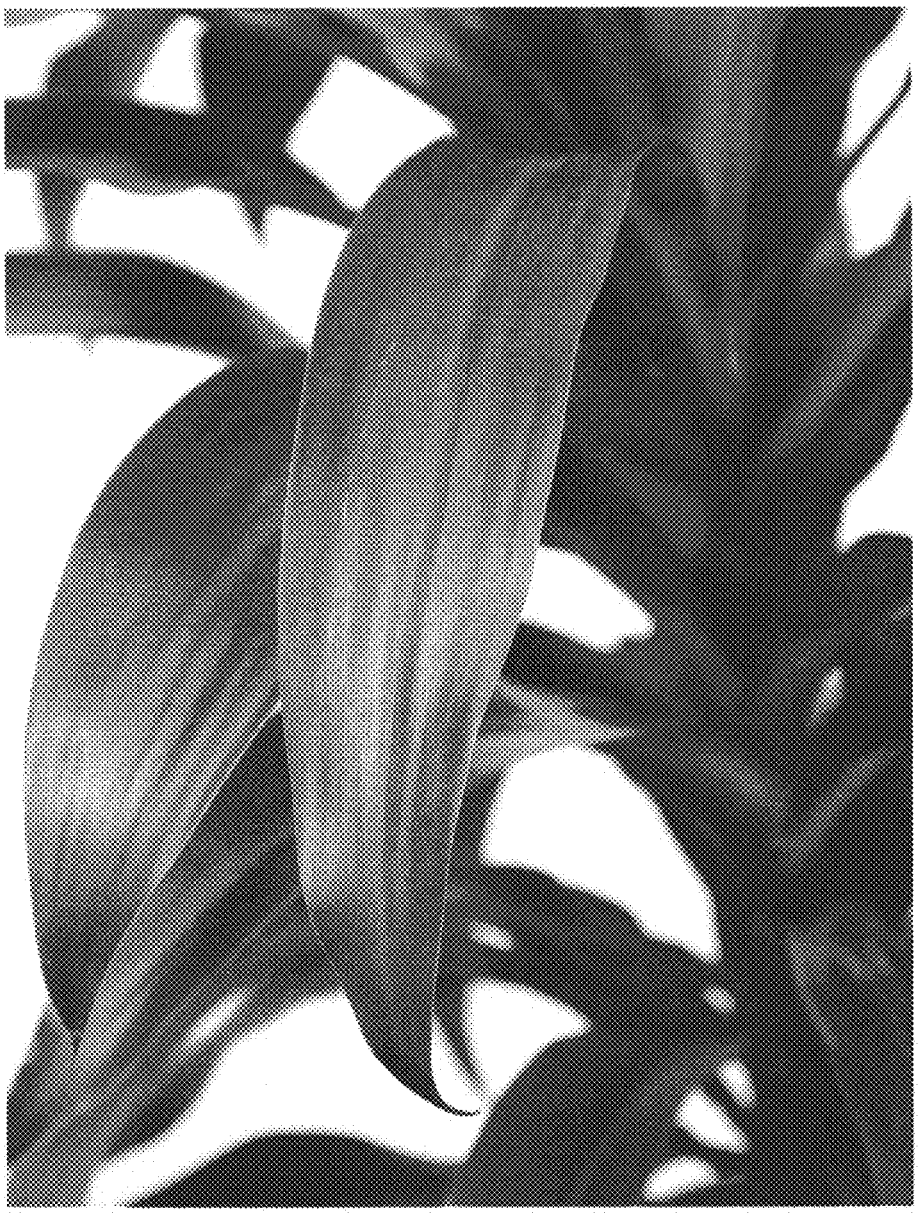
FIG. 2 illustrates, as nearly true as it is reasonably possible to make the same in color photographs of this type, the typical foliage of 'PVDRALC'.
Figure 3:
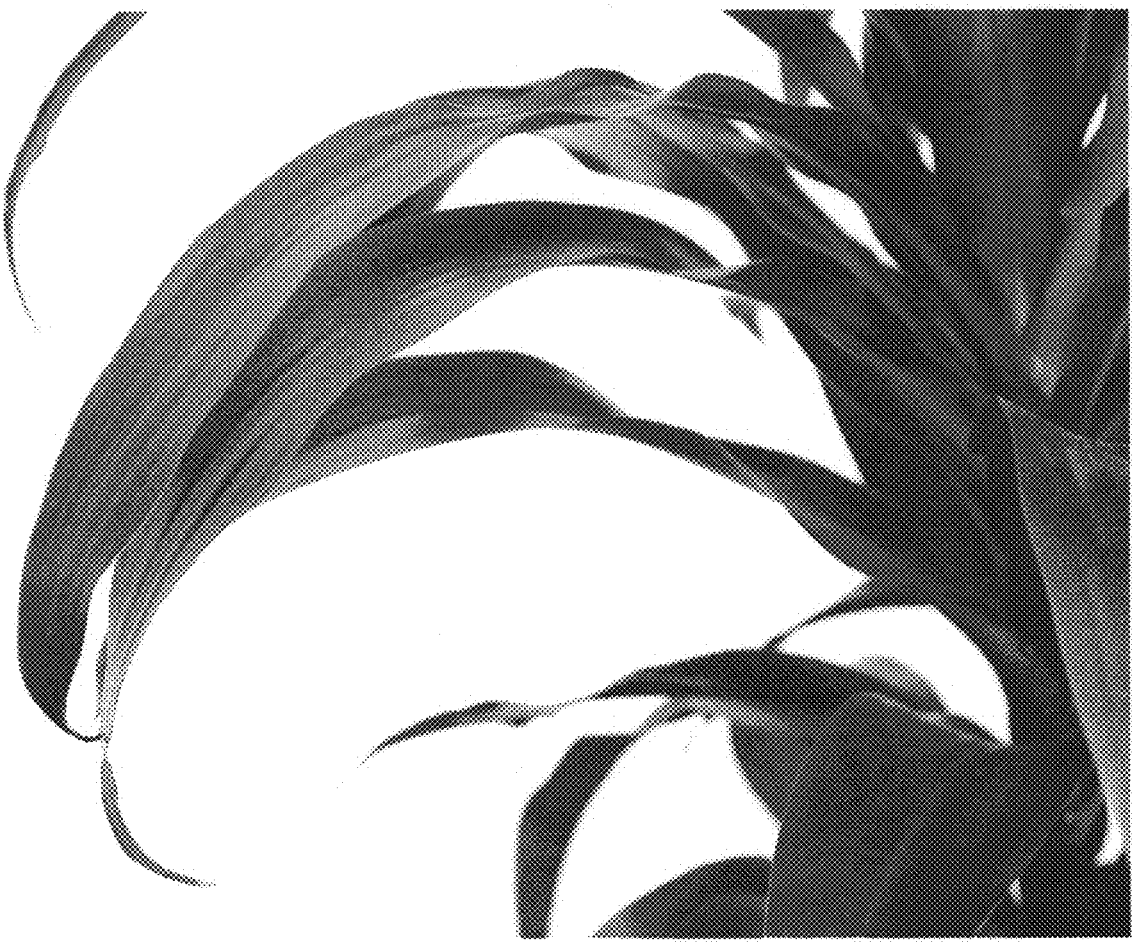
FIG. 3 illustrates, as nearly true as it is reasonably possible to make the same in color photographs of this type, the typical lower foliage of 'PVDRALC', shown from an alternate perspective.

The following observations and measurements, made in May of 2019, describe averages from a sample set of six specimens of 26 week-old 'PVDRALC' plants grown in 15 cm nursery pots in San Jose, Costa Rica. Plants were produced using conventional greenhouse production protocols for *Dracaena* sp. which consisted of growing under shade cloth, irrigating at regular intervals with ebb and flow flood benches, and fertigation. No chemical treatments of any kind were utilized.

Those skilled in the art will appreciate that certain characteristics will vary with older or, conversely, with younger plants. 'PVDRALC' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'PVDRALC' and comparisons with the parent plant and most similar commercial *Dracaena* cultivar known to the inventor are provided below.

Plant description:

*Growth habit*.—Upright evergreen perennial with foliage born on a solitary unbranched stem.

*Plant profile*.—Broad oblong.

*Average height from base to top of foliage*.—72.5 cm.

*Average width*.—Average of 75.0 cm.

*Growth rate*.—Moderately fast growing.

*Plant vigor*.—Highly vigorous.

*Propagation details*.—Asexual propagation is accomplished by stem cuttings.

*Time to initiate roots*.—Approximately 5 weeks are required to initiate roots at 25 degrees Celsius.

*Time to produce a marketable* 15 *cm potted plant*.—Approximately 15 to 30 weeks. Pinching will increase lateral branching.

*Disease and pest resistance or susceptibility*.—Neither tolerance nor resistance to normal diseases and pests of *Dracaena fragrans* have been observed.

*Environmental tolerances*.—Adapt to USDA Hardiness Zones 10 through 12 and temperatures as high as 40 degrees Celsius; moderate tolerance to rain and wind.

Root system:

*General*.—Fibrous; freely branched and moderately dense rooting.

*Distribution in the soil profile*.—Shallow to moderately deep.

*Texture*.—Smooth; glabrous.

*Color*.—Greyed-orange, RHS N170A.

Stems:

*Branching characteristics*.—Not freely branched in nature; develops lateral branches only when manipulated by man by way of pruning. Naturally produces one main stem arising from the plant's base.

*Attitude*.—Near vertical.

*Strength*.—Very strong.

*Length*.—47.8 cm.

*Diameter*.—Average 1.8 cm.

*Internode length*.—Average 0.8 cm.

*Stem texture*.—Glabrous; smooth.

*Stem luster*.—Matte.

*Color, developing stems*.—Yellow-Green, nearest to RHS 145C.

*Color, mature stems*.—Yellow-Green, nearest to in between RHS 145B and 147D.

*Color at the internodes*.—Yellow-Green, nearest to a mixture of RHS 146C and 146D.

Foliage:

*Arrangement*.—Spiraled.

*Attachment*.—Sheathed.

*Division*.—Simple.

*Attitude*.—Foliage near the apex is upright to outward and becomes progressively more relaxed towards the base.

*Number of leaves per lateral branch*.—44.

*Lamina*.—Dimensions — 46.1 cm long and 8.4 cm wide, on average. Shape — Lorate. Aspect — Flat and curled downward with the distalmost portion on the lamina pointing yet further downward at an average angle of minus −135 degrees to the rest of the lamina. Apex — Acute with a short, soft but pointed tip. Base — Sheathed. Sheath — Length — 4.5 cm. Width — 1.9 cm. Color, adaxial surface — Green-white, nearest to RHS 157A. Color, abaxial surface — Green, nearest to RHS 143C. Margin — Entire; not undulate to very lightly undulate. Texture and luster of adaxial surface — Smooth, glabrous and moderately glossy. Texture and luster of abaxial surface — Smooth, glabrous and slightly glossy. Color — Juvenile foliage, adaxial surface — Green, nearest to in between RHS NN137A and 139A. Juvenile foliage, abaxial surface — Green, nearest to RHS 143A. Mature foliage, adaxial surface — Nearest to in between yellow-green and greyed-green, RHS 147A and N189A. Mature foliage, abaxial surface — Green, nearest to RHS NN137B, and fading to in between a darker shade of green and yellow-green towards the margins, RHS NN137A and 147A. Venation — Pattern — Parallel. Color, adaxial surface — The main vein nearest green, nearest to RHS 137B. All other veins are indistinguishable from the surrounding foliage: nearest to in between yellow-green and greyed-green, RHS 147A and N189A. Color, abaxial surface — The main vein is yellow-green, nearest to a mixture of RHS 146A and 146B. All other veins are indistinguishable from the surrounding foliage: green, nearest to RHS NN137B, and fading to in between a darker shade of green and yellow-green towards the margins, RHS NN137A and 147A.

Inflorescence: To date, flowering has not been observed.

Flower buds: To date, flowering has not been observed.

Flower: To date, flowering has not been observed.

Reproductive organs: To date, flowering has not been observed.

Seed and fruit: To date, flowering has not been observed.

COMPARISONS WITH THE PARENT PLANT

Plants of the new cultivar 'PVDRALC' may be distinguished from its parent, *Dracaena fragrans* 'Steudneri' plant (not patented), by the characteristics described in Table 1.

TABLE 1

| Characteristic | 'PVDRALC' | 'Steudneri' |
|---|---|---|
| Growth habit. | Less compact. | More compact. |
| Foliage attitude. | Foliage is generally more relaxed. | Foliage is generally more upright. |
| Foliage aspect. | Less spiraled (i.e. axially twisted) | More spiralled. |
| Foliage margins. | Less undulate. | More undulate. |
| General coloration of the foliage. | Darker shade of green than the parent. | Medium green. |

Plants of the new cultivar 'PVDRALC' may be distinguished from the closest known commercial comparator, *Dracaena fragrans* 'Golden Coast' (not patented), by the characteristics described in Table 2.

TABLE 2

| Characteristic | 'PVDRALC' | 'Golden Coast' |
|---|---|---|
| Foliage attitude. | Foliage is generally more relaxed. | Foliage is generally more upright. |
| Foliage margins. | Undulate. | No undulation. |
| Internode length. | Longer internodes compared to *Dracaena steudneri*. | Shorter internodes compared to 'PVDRALC'. |
| General coloration of the foliage. | Darker shade of green than the parent. | Green foliage with broad, light green to light yellow axial striations towards the margins; narrowly margined yellow. |

That which is claimed is:

1. A new and distinct cultivar of *Dracaena* plant named 'PVDRALC', substantially as described and illustrated herein.

* * * * *